United States Patent [19]

Black et al.

[11] Patent Number: 5,591,753
[45] Date of Patent: Jan. 7, 1997

[54] COMBINATION TREATMENT FOR OSTEOPOROSIS

[75] Inventors: Larry J. Black, Indianapolis; George J. Cullinan, Trafalgar, both of Ind.

[73] Assignee: Eli Lilly and Company, Indianapolis, Ind.

[21] Appl. No.: 189,399

[22] Filed: Jan. 28, 1994

[51] Int. Cl.⁶ .................... A61K 31/445; A61K 31/415; A61K 31/38
[52] U.S. Cl. .................... 514/324; 514/397; 514/443
[58] Field of Search .................... 514/324, 397, 514/443

[56] References Cited

U.S. PATENT DOCUMENTS

| | | |
|---|---|---|
| 4,133,814 | 1/1979 | Jones et al. |
| 4,380,635 | 4/1983 | Peters . |
| 4,418,068 | 11/1983 | Jones . |
| 5,075,321 | 12/1991 | Schreiber . |

FOREIGN PATENT DOCUMENTS

| | | |
|---|---|---|
| WO93/10113 | 5/1993 | Japan . |
| WO93/1074 | 6/1993 | WIPO . |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am Soc. Bone & Min. Res., Tampa, Sep. 18–22, 1993.

Sato et al., "DEXA Analysis of Raloxifene Effects on the Bones From Ovariectomzed Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB-3 Expression in Bone;" .Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L. J. "Biological Actions and Binding Properties of a New Estrogen Antagosist LY117018," In: Homone Antagonists, 129–82, 1982 (M. K. Agarwal ed.) Walter de Gruyter and Co., Berlin New York.

(List continued on next page.)

*Primary Examiner*—Zohreh Fay
*Attorney, Agent, or Firm*—James J. Sales

[57] ABSTRACT

This invention provides a new method for treating osteoporosis comprising administering:

1) a compound of formula I

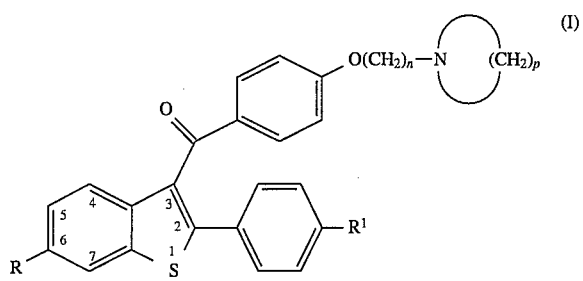

wherein

R and $R^1$, independently, are hydrogen, hydroxyl, $C_1$–$C_6$-alkoxy, $C_1$–$C_6$ acyloxy, $C_1$–$C_6$ alkoxy-$C_2$–$C_6$-acyloxy, $R^2$-substituted aryloxy, $R^2$-substituted aroyloxy, $R^3$-substituted carbonyloxy or halo;

$R^2$ is $C_1$–$C_3$-alkyl, $C_1$–$C_3$-alkoxy, hydrogen or halo; and $R^3$ is $C_1$–$C_6$-alkoxy or aryloxy;

n is 2, 3 or 4; and p is 4, 5 or 6;

or a pharmaceutically acceptable salt or solvate thereof; together with 2) a progestin selected from medroxyprogesterone, norethindrone or norethynodrel, or a pharmaceutically acceptable salt thereof; in amounts such that the combination retains or increases bone density.

The invention also provides pharmaceutical formulations for inhibiting bone loss comprising (1) a compound of formula I, or a pharmaceutically acceptable salt or solvate thereof; and (2) a progestin selected from medroxyprogesterone, norethindrone or norethynodrel, or a pharmaceutically acceptable salt thereof; in amounts such that the combination inhibits bone loss, together with one or more pharmaceutically acceptable carriers.

6 Claims, No Drawings

OTHER PUBLICATIONS

Black et al., LY156758: A Unique Antiestrogen Displaying High Affinity for Estrogen Receptors, Negligible Estrogenic Acitvity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2 (4–methoxyphenyl)–1–napthalenyl] [4–[2–pyrrolidinyl) ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo [b] thiophene Derivatives Leading to [6–Hydroxy–2–(4–hydroxyphenyl) benzo [b] thien–3–y1] [4–[2–(1–piperidinyl) ethoxy]–phenyl] methanone Hydrochloride (LY156758), a Remarkably Effective Estrogen Antagonist with Only Minimal Intrinsic Estrogenicity, J. Med. Chem. 27(8), 1984, 1057–1066.

Bain et al., High Dose Gestagens Modulate Bone Resorption and formation and Enhance Estrogen–Induced Endosteal Bone formation in the Ovariectomized Mouse, *J. of Bone and Mineral Research*, 8, 219–230 (Nov. 2, 1993).

COMBINATION TREATMENT FOR OSTEOPOROSIS

BACKGROUND OF THE INVENTION

Osteoporosis describes a group of diseases which arise from diverse etiologies, but which are characterized by the net loss of bone mass per unit volume. A consequence of this loss of bone mass is the failure of the skeletal frame to provide adequate structural support for the body, resulting in bone fracture. One of the most common types of osteoporosis occurs in women shortly after menopause. Most women lose between 20–60% of the bone mass in the trabecular compartment of the bone within 3–6 years after the cessation of menses. This rapid loss of bone loss is generally associated with an increase of both bone resorption and formation. The resorptive cycle is more dominant, however; and the result is a net loss of bone mass.

Thus, osteoporosis is a common and serious disease among post-menopausal women. An estimated 25 million women in the United States alone are afflicted with this disease. The results of this disease are both personally and economically harmful.

Large economic losses are due to its chronic nature and the need for extensive and long term support (hospitalization and nursing home care) from the disease sequellae. The losses are especially great in more elderly patients. Additionally, although osteoporosis is not generally considered a life threatening condition, there is a 20–30% mortality rate related to hip fractures in elderly women. A large percentage of this mortality rate can be directly associated with post-menopausal osteoporosis.

The tissue in the bone most vulnerable to the effects of post-menopausal osteoporosis is the trabecular bone. This tissue is often referred to as spongy or cancellous bone and is particularly concentrated near the ends of the bone, near the joints and in the vertebrae of the spine. Trabecular tissue is characterized by small osteoid structures which interconnect with each other and with the more solid and dense cortical tissue that makes up the outer surface and central shaft of the bone. This criss-cross network of trabeculae gives lateral support to the outer cortical structure and is critical to the bio-mechanical strength of the overall structure. It is primarily the net resorption and loss of the trabeculae which leads to the failure and fracture of bone in post-menopausal osteoporosis. In light of the loss of the trabeculae in post-menopausal women, it is not surprising that the most common fractures are those associated with bones which are highly dependent on trabecular support, e.g., the vertebrae, the neck of the weight bearing bones (femur) and the forearm. Indeed, hip fracture, collies fractures, and vertebral crush fractures are hall-marks of post-menopausal osteoporosis.

A very important concept in the treatment and study of post-menopausal osteoporosis is the concept of fracture threshold. The fracture threshold is the point at which the bone density (therefore, the bone strength) decreases to a value where there is a high probability of bone fracture. This point is not a particular value for all women but rather a relative number for an individual and is dependent on a number of factors such as weight, life-style, or other risks which might contribute to the possibility of bone fracture.

In general, most pre-menopausal women have bone densities above the fracture threshold, and there is a low probability that a fracture will occur. A woman's pre-menopausal bone density and the rate of bone loss after menopause will determine when, or if, she will cross the threshold and be at risk for fracture. For women who present with fractures due to osteoporosis, ideal therapy would be to increase bone density (strength) to a value above the fracture threshold. Alternatively, for women whose bone density is still above the threshold, it would be advantageous to keep them above it.

Today, the only available effective treatment for post-menopausal osteoporosis is hormone replacement therapy, specifically estrogen replacement because post-menopausal women are estrogen deficient. The mechanism of action of estrogen in the treatment of osteoporosis is not well understood; however, it is generally agreed that it inhibits bone resorption. The net effect of the estrogen replacement therapy (ERT) is to keep the woman's bone density at the level at which therapy was initiated, i.e., it maintains bone density. If a woman is above the fracture threshold when (ERT) is initiated, and if ERT is maintained, she will remain above the threshold and be at low risk for fracture. This fact would argue for the placement of women on ERT at or soon after the cessation of menses.

For women whose bone density has already fallen below the fracture threshold, however, ERT will only maintain bone density at the level at which they began therapy. Thus, these women will remain below the threshold and will be at further risk for fracture. ERT is still advisable for these women because it will keep a bad situation from getting worse. It would clearly be advantageous, however, to have a therapy which would boost bone density above the fracture threshold to more normal levels and then maintain it. Currently, there are no effective approved therapies which demonstrate an ability to increase bone density to such a level.

As noted, ERT is now the only effective approved treatment for post-menopausal osteoporosis. In those women who do not have a uterus, estrogen (usually given as a conjugated form of estrone) can be given by itself. In most post-menopausal women who have a uterus, however, unopposed estrogen increases the risk of endometrial cancer. Thus, a progestin is often also administered, either as a combination or in cyclical therapy, to reduce that risk.

"Antiestrogen" is a term that "has been rather broadly applied to several different types of compounds that inhibit or modify the action of estrogen. Progestins and androgens have been described as antiestrogenic . . ." (Goodman and Gilman, *The Pharmacological Basis of Therapeutics*, 6th Ed., p 1431.) In addition, certain synthetic compounds, such as tamoxifene, clomiphene, raloxifene and nafoxidine, are called antiestrogens and have been shown both experimentally and clinically to block some of the effects of estrogen. The synthetic "antiestrogens" were principally developed for the treatment of estrogen-dependent breast carcinoma. These compounds are classical mixed agonist/antagonists which demonstrate some estrogenic activity. For example, tamoxifene, the most widely used antiestrogen, has been shown to have estrogenic effects in humans.

Recently, the "antiestrogen" group typified by raloxifene (formerly called keoxifene) has been shown to inhibit bone loss in animal experiments, indicating that these compounds should be useful in the treatment of post-menopausal osteoporosis. (See our copending application entitled, METHODS FOR INHIBITING BONE LOSS, Ser. No. 07/920,933, filed Jul. 28, 1992).

We have now discovered that administering a raloxifene-type compound of formula I together with certain progestins can return bone density to nearly normal levels, an effect which neither agent is capable of doing alone.

SUMMARY OF THE INVENTION

This invention provides a new method for treating osteoporosis comprising administering:

1) a compound of formula I

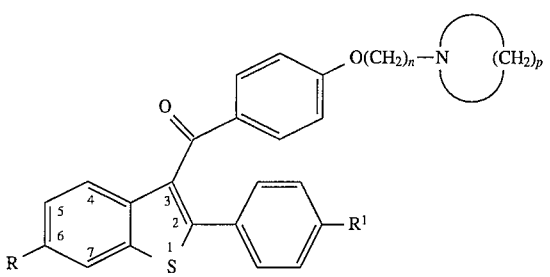

wherein

R and $R^1$, independently, are hydrogen, hydroxyl, $C_1$–$C_6$-alkoxy, $C_1$–$C_6$ acyloxy, $C_1$–$C_6$ alkoxy-$C_2$–$C_6$-acyloxy, $R^2$-substituted aryloxy, $R^2$-substituted aroyloxy, $R^3$-substituted carbonyloxy or halo;

$R^2$ is $C_1$–$C_3$-alkyl, $C_1$–$C_3$-alkoxy, hydrogen or halo; and $R^3$ is $C_1$–$C_6$-alkoxy or aryloxy;

n is 2, 3 or 4; and p is 4, 5 or 6;

or a pharmaceutically acceptable salt or solvate thereof; together with 2) a progestin selected from medroxyprogesterone, norethindrone or norethynodrel, or a pharmaceutically acceptable salt thereof; in amounts such that the combination retains or increases bone density.

The invention also provides pharmaceutical formulations for inhibiting bone loss comprising (1) a compound of formula I, or a pharmaceutically acceptable salt or solvate thereof; and (2) a progestin selected from medroxyprogesterone, norethindrone or norethynodrel, or a pharmaceutically acceptable salt thereof; in amounts such that the combination inhibits bone loss, together with one or more pharmaceutically acceptable carriers.

DETAILED DESCRIPTION OF THE INVENTION

This invention concerns the discovery that combination therapy comprising administering one component from a group of 2-phenyl-3-aroylbenzothiophenes (benzothiophenes) of formula I together with a second component that is a progestin selected from medroxyprogesterone, norethindrone or norethynodrel is especially useful in the treatment of osteoporosis. Taken alone, the benzothiophenes of formula I inhibit the loss of bone that occurs in those afflicted with osteoporosis, but cannot increase bone density to return to the normal levels before the disease process started. When administered in conjunction with a selected progestin, however, the combination can not only maintain bone density, but increase it to more normal levels ("normalize" it). As discussed supra, post-menopausal osteoporosis results from a lack of endogenous estrogen such as occurs in women following cessation of menstruation due to natural, surgical, or other processes. The reduction of bone density and mass that more rarely occurs in men is also tied to the loss of hormonal regulation and is, therefore, also a target for therapy according to the methods of the current invention.

The general chemical terms used in the description of a compound of formula I have their usual meanings. For example, the term "$C_1$–$C_3$-alkyl" includes methyl, ethyl, propyl and isopropyl.

The term "$C_1$–$C_6$-alkoxy" includes methoxy, ethoxy, propoxy, butoxy, pentyloxy and hexyloxy, and also includes branched chain structures such as, for example, isopropoxy and isobutoxy.

The term "$C_1$–$C_6$-acyloxy" includes acetoxy, ethanoyloxy, propanoyloxy, butanoyloxy, pentanoyloxy, hexanoyloxy, and the like and also includes branched chain structures such as, for example, 2,2-dimethylpropanoyloxy and 3,3-dimethylbutanoyloxy.

The term "$C_1$–$C_6$-alkoxy-$C_2$–$C_6$-acyloxy" contemplates, for example, methoxyethanoyloxy, methoxypropanoyloxy, methoxybutanoyloxy, methoxy-pentanoyloxy, methoxyhexanoyloxy, ethoxyethanoyloxy, ethoxypropanoyloxy, ethoxybutanoyloxy, ethoxypentanoyloxy, ethoxyhexanoyloxy, propoxyethanoyloxy, propoxypropanoyloxy, propoxybutanoyloxy and the like.

As used herein, references to alkyl and alkoxy structures also include cycloalkyl and cycloalkoxy groups where the number of carbons within the structure is at least 3.

The terms "$R^2$-substituted aryloxy" and "$R^2$-substituted aroyloxy" include such groups as phenyloxy, thienyloxy, furyloxy, naphthyloxy, benzoyloxy, thienoyloxy, furoyloxy, naphthoyloxy, and the like, where the $R^2$ substitution group may be hydrogen, hydroxyl, $C_1$–$C_3$-alkyl, $C_1$–$C_3$-alkoxy or halo.

The term "$R^3$-substituted carbonyloxy, where the $R^3$ substitution group may be $C_1$–$C_6$-alkoxy or aryloxy, includes carbonate structures such as methoxycarbonyloxy ethoxycarbonyloxy, propoxycarbonyloxy, butoxycarbonyloxy, pentyloxycarbonyloxy, hexyloxycarbonyloxy, phenyloxycarbonyloxy, thienyloxycarbonyloxy, furyloxycarbonyloxy and naphthyloxycarbonyloxy.

Raloxifene is the following compound:

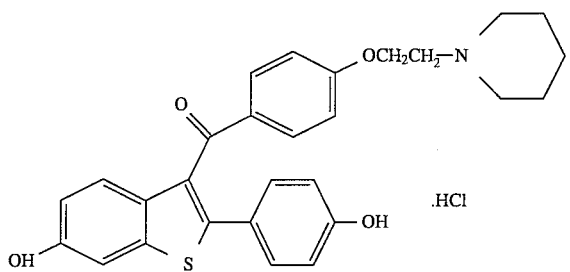

Preferred methods and formulations of this invention comprise the use of a formula I compound wherein R and $R^1$ are hydroxyl, $C_1$–$C_6$-acyloxy, $C_1$–$C_6$-alkoxy-$C_2$–$C_6$-acyloxy, $R^2$-substituted-aroyloxy or $R^3$-substituted carbonyloxy, the latter groups representing ester and carbonate configurations; and the selected progestin is norethindrone or norethynodrel. Other preferred methods include the use of a formula I compound wherein R and $R^1$ are the same; n is 2 and p is 5 or 6; and the selected progestin is norethindrone or norethynodrel.

An especially preferred method includes the use of a formula I compound wherein R and $R^1$ are hydroxyl, n is 2 and p is 4 or 5; and the selected progestin is norethindrone. A most preferred embodiment of the invention involves the use of raloxifene, especially when administered as the hydrochloride salt, and norethynodrel.

The formula I compounds used in the methods of the current invention can be made according to established procedures, such as those detailed in U.S. Pat. Nos. 4,133, 814 and 4,418,068 and pending application Ser. No. 07/920, 933 filed Jul. 28, 1992, all incorporated herein by reference. In general, the process starts with a benzo[b]thiophene having a 6-hydroxyl group and a 2-(4-hydroxyphenyl) group. The starting compound is protected, acylated or alkylated, and deprotected to form the formula I compounds wherein R and $R^1$ are both hydroxy. The formula I compounds that are ethers, esters and carbonates may then be formed if desired. Examples of the preparation of such compounds are provided in the U.S. patents discussed supra. Modifications to these methods may be necessary to accommodate reactive functionalities of particular substituents. Such modifications would be apparent to those skilled in the art.

The formula I compounds form acid and base addition salts with a wide variety of organic and inorganic acids and bases and include the physiologically acceptable salts which are often used in pharmaceutical chemistry. Such salts may also be used in the methods and formulations of this invention.

Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methane-sulfonate, naphthalene-1-sulfonate, naphthalene-2-sulfonate, p-toluenesulfonate, xylenesulfonate, tartrate, and the like.

The acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides and carbonates as well as aliphatic and aromatic amines, aliphatic diamines and hydroxy alkylamines. Bases especially useful in the preparation of addition salts include ammonium hydroxide, potassium carbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

In addition, some of the formula I compounds may form solvates with water or organic solvents such as ethanol. These solvates are also contemplated for use in the methods and formulations of this invention.

This invention also provides pharmaceutical formulations useful for inhibiting bone loss comprising (1) a formula I compound or a pharmaceutically acceptable salt or solvate thereof; (2) a progestin selected from medroxyprogesterone, norethindrone or norethynodrel, or a pharmaceutically acceptable salt thereof; and (3) one or more pharmaceutically acceptable excipients.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethylene glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosages of the formula I compound and the selected progestin required to treat osteoporosis or inhibit bone loss according to this invention will depend upon the severity of the disease, its route of administration, and related factors that will be decided by the attending physician. Generally, an effective dose of the formula I compound will be from about 0.1 to about 1000 mg, typically from about 50 to about 400 mg, and most preferably about 50 to about 200 mg. Generally, an effective dose of the selected progestin will be from about 0.01 to about 500 mg, and preferably from about 1 to about 200 mg. Dosages will be administered to a subject in need of treatment from once to about three times each day, or more often as needed to effectively inhibit the bone loss process.

EXAMPLE 1

In these examples, a model of post-menopausal osteoporosis was used in which effects of different treatments upon femur density were determined.

Seventy-five day old female Sprague Dawley rats (weight range of 225 to 275 g) were obtained from Charles River Laboratories (Portage, Mich.). They were housed in groups of 3 and had ad libitum access to food (calcium content approximately 1%) and water. Room temperature was maintained at 22.2°±1.7° C. with a minimum relative humidity of 40%. The photoperiod in the room was 12 hours light and 12 hours dark.

One week after arrival, the rats underwent bilateral ovariectomy under anesthesia (44 mg/kg Ketamine and 5 mg/kg Xylazine (Butler, Indianapolis, Ind.) administered intramuscularly). Treatment with vehicle or the indicated compound was initiated either on the day of surgery following recovery from anesthesia or 35 days following the surgery.

Oral dosage was by gavage in 0.5 mL of 1% carboxymethylcellulose (CMC).

Body weight was determined at the time of surgery and weekly during the study, and the dosage was adjusted with changes in body weight. Vehicle-treated ovariectomized (ovex) rats and non-ovariectomized (intact) rats were evaluated in parallel with each experimental group to serve as negative and positive controls.

The rats were treated daily for 35 days (6 rats per treatment group) and sacrificed by decapitation on the 36th day. The 35-day time period was sufficient to allow maximal reduction in bone density, measured as described infra. At the time of sacrifice, the uteri were removed, dissected free of extraneous tissue, and the fluid contents were expelled before determination of wet weight in order to confirm estrogen deficiency associated with complete ovariectomy. Uterine weight was routinely reduced about 75% in response to ovariectomy. The uteri were then placed in 10% neutral buffered formalin to allow for subsequent histological analysis.

The right femurs were excised and scanned at the distal metaphysis 1 mm from the patellar groove with single photon absorptiometry. Results of the densitometer measurements represent a calculation of bone density as a function of the bone mineral content and bone width. (EE2=ethynyl estradiol; RAL=Raloxifene).

| Compound(s) | Bone Density |
| --- | --- |
| Trial 1 | |
| A) EE2 (100 µg/kg) | 28.270 |
| B) Ovex (No compound) | 8.033 |
| C) Intact (No compound) | 42.403 |
| D) Provera (10 mg/kg) | 34.132 |
| E) Ral (0.01 mg/kg) | 4.823 |
| F) Ral (0.1 mg/kg) | 2.928 |
| G) Ral (1 mg/kg) | 15.400 |
| H) Ral 10 mg/kg | 18.017 |
| I) D + E | 36.820 |
| J) D + F | 38.902 |
| K) D + G | 51.935 |
| L) D + H | 61.528 |
| Trial 2 | |
| A) EE2 (100 µg/kg) | 53.122 |
| B) Ovex (No compound) | 25.918 |
| C) Intact (No compound) | 49.627 |
| D) Norethindrone (10 mg/kg) | 42.087 |
| E) Ral (0.01 mg/kg) | 15.672 |
| F) Ral (0.10 mg/kg) | 30.265 |
| G) Ral (1 mg/kg) | 46.237 |
| H) Ral 10 mg/kg | 35.765 |
| I) D + E | 38.795 |
| J) D + F | 53.122 |
| K) D + G | 59.155 |
| L) D + H | 57.485 |
| Trial 3 | |
| A) EE2 (100 µg/kg) | 46.670 |

-continued

| Compound(s) | Bone Density |
| --- | --- |
| B) Ovex (No compound) | 20.340 |
| C) Intact (No compound) | 47.867 |
| D) Norethynodrel (10 mg/kg) | 35.563 |
| E) Ral (0.01 mg/kg) | 11.208 |
| F) Ral (0.1 mg/kg) | 19.693 |
| G) Ral (1 mg/kg) | 30.012 |
| H) Ral (10 mg/kg) | 30.325 |
| I) D + E | 43.948 |
| J) D + F | 37.777 |
| K) D + G | 54.773 |
| L) D + H | 42.283 |
| Trial 4 | |
| A) EE2 (100 µg/kg) | 59.802 |
| B) Ovex (No compound) | 33.538 |
| C) Intact (No compound) | 68.317 |
| D) Norgesterol (10 mg/kg) | 38.895 |
| E) Ral (0.01 mg/kg) | 28.363 |
| F) Ral (0.10 mg/kg) | 56.207 |
| G) Ral (1 mg/kg) | 45.712 |
| H) Ral 10 mg/kg | 51.533 |
| I) D + E | 26.328 |
| J) D + F | 48.057 |
| K) D + G | 38.270 |
| L) D + H | 53.903 |
| Trial 5 | |
| A) EE2 (100 µg/kg) | 50.700 |
| B) Ovex (No compound) | 26.700 |
| C) Intact (No compound) | 28.545 |
| D) Provera (10 mg/kg) | 60.832 |
| E) *Compound A (1 mg/kg) | 34.650 |
| F) Compound A (10 mg/kg) | 48.688 |
| G) D + E | 61.273 |
| H) D + F | 58.472 |

*Compound A is the hydrochloride salt of a compound of formula 1 wherein $n = 2$, $p = 5$, and R and $R^1$ are both

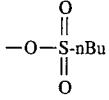

| Trial 6 | |
| --- | --- |
| A) EE2 (100 µg/kg) | 50.700 |
| B) Ovex (No compound) | 26.700 |
| C) Intact (No compound) | 28.545 |
| D) Provera (10 mg/kg) | 60.832 |
| E) *Compound B (1 mg/kg) | 37.937 |
| F) Compound B (10 mg/kg) | 42.873 |
| G) D + E | 75.498 |
| H) D + F | 68.163 |

*Compound B is the hydrochloride salt of a compound of formula 1 wherein $n = 2$, $p = 5$, and R and $R^1$ are both

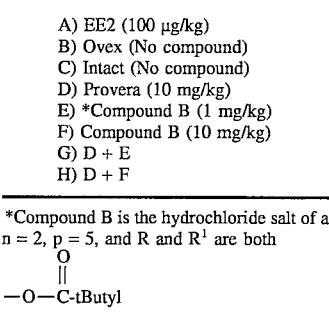

We claim:

1. A method for treating osteoporosis comprising administering:

1) a compound of formula I

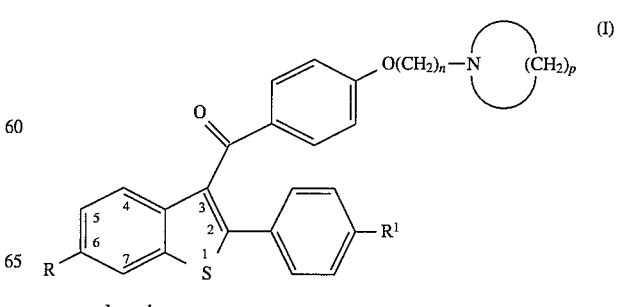

wherein

R and $R^1$, independently, are hydrogen, hydroxyl, $C_1$–$C_6$-alkoxy, $C_1$–$C_6$ acyloxy, $C_1$–$C_6$ alkoxy-$C_2$–$C_6$-acyloxy, $R^2$-substituted aryloxy, $R^2$-substituted aroyloxy, $R^3$-substituted carbonyloxy or halo;

$R^2$ is $C_1$–$C_3$-alkyl, $C_1$–$C_3$-alkoxy, hydrogen or halo; and $R^3$ is $C_1$–$C_6$-alkoxy or aryloxy;

n is 2, 3 or 4; and p is 4, 5 or 6;

or a pharmaceutically acceptable salt or solvate thereof; together with 2) a progestin selected from medroxyprogesterone, norethindrone or norethynodrel, or a pharmaceutically acceptable salt thereof; in amounts such that the combination retains or increases bone density.

2. A method of claim 1 wherein the formula I compound is one in which R and $R^1$ are selected from hydroxyl, $C_1$–$C_6$-acyloxy, $C_1$–$C_6$-alkoxy-$C_2$–$C_6$-acyloxy, $R^2$-substituted-aroyloxy or $R^3$-substituted carbonyloxy and the selected progestin is norethindrone or norethynodrel.

3. A method of claim 2 wherein the formula I compound is one in which R and $R^1$ are hydroxyl, n is 2 and p is 4 or 5; and the selected progestin is norethindrone.

4. A method of claim 3 wherein the formula I compound is one in which p is 5.

5. A method of claim 2 wherein R and $R^1$ are hydroxyl, n is 2 and p is 5; and the selected progestin is norethynodrel.

6. A method of claim 1 wherein the amount of formula I compound administered is from 0.1 to about 1000 mg/kg of body weight and the amount of selected progestin administered is from about 0.01 to about 500 mg/kg of body weight.

* * * * *